US008173108B2

(12) United States Patent
Misso et al.

(10) Patent No.: US 8,173,108 B2
(45) Date of Patent: *May 8, 2012

(54) SUNSCREEN COMPOSITION

(75) Inventors: Luis Roberto Misso, Stratford, CT (US); Jack Polonka, Peekskill, NY (US)

(73) Assignee: Conopco, Inc., Englewood Cliffs, NJ (US)

( * ) Notice: Subject to any disclaimer, the term of this patent is extended or adjusted under 35 U.S.C. 154(b) by 345 days.

This patent is subject to a terminal disclaimer.

(21) Appl. No.: 12/611,941

(22) Filed: Nov. 4, 2009

(65) Prior Publication Data

US 2011/0104086 A1    May 5, 2011

(51) Int. Cl.
*A61K 8/00* (2006.01)
*A61Q 17/04* (2006.01)
(52) U.S. Cl. ............... 424/60; 424/59; 514/394
(58) Field of Classification Search .................. None
See application file for complete search history.

(56) References Cited

U.S. PATENT DOCUMENTS

| | | | |
|---|---|---|---|
| 4,585,597 A | 4/1986 | Lang et al. | |
| 5,041,281 A | 8/1991 | Strobridge | |
| 5,099,013 A | 3/1992 | Balazs et al. | |
| 5,116,601 A | 5/1992 | Mondet et al. | |
| 5,182,407 A | 1/1993 | Sebag | |
| 5,470,551 A | 11/1995 | Dubief et al. | |
| 5,626,840 A | 5/1997 | Thomaides et al. | |
| 5,667,765 A | 9/1997 | Hansenne et al. | |
| 5,680,962 A * | 10/1997 | McEleney et al. | 222/144.5 |
| 5,709,850 A | 1/1998 | Mondet et al. | |
| 5,753,215 A | 5/1998 | Mougin et al. | |
| 5,759,524 A * | 6/1998 | Tanner et al. | 424/59 |
| 5,830,438 A | 11/1998 | Dupuis | |
| 5,961,961 A | 10/1999 | Dobkowski et al. | |
| 5,968,494 A | 10/1999 | Kukkala et al. | |
| 6,083,492 A | 7/2000 | Modi | |
| 6,153,176 A | 11/2000 | Kaleta et al. | |
| 6,261,575 B1 * | 7/2001 | Hoppe et al. | 424/401 |
| 6,337,077 B1 | 1/2002 | Chevalier et al. | |
| 6,440,401 B1 | 8/2002 | Heywang et al. | |
| 6,485,713 B1 | 11/2002 | Bonda et al. | |
| 7,014,842 B2 | 3/2006 | Dueva-Koganov et al. | |
| 7,244,416 B2 | 7/2007 | Meyer et al. | |
| 7,465,460 B1 | 12/2008 | Gross | |
| 2002/0176834 A1 | 11/2002 | Adams et al. | |
| 2003/0191271 A1 | 10/2003 | Mondet et al. | |
| 2004/0228814 A1 | 11/2004 | Candau et al. | |
| 2004/0228815 A1 | 11/2004 | L'Alloret | |
| 2004/0241112 A1 | 12/2004 | Evison et al. | |
| 2004/0258636 A1 | 12/2004 | Richard et al. | |
| 2005/0025736 A1 | 2/2005 | Jachowicz et al. | |
| 2007/0074356 A1 | 4/2007 | Lalleman | |
| 2007/0142255 A1 | 6/2007 | Qiu | |
| 2008/0181858 A1 | 7/2008 | Davis et al. | |
| 2008/0193395 A1 | 8/2008 | Viala et al. | |
| 2008/0199526 A1 | 8/2008 | Poschalko et al. | |
| 2008/0287537 A1 | 11/2008 | Dalko | |

FOREIGN PATENT DOCUMENTS

| | | |
|---|---|---|
| DE | 202008017353 U1 | 6/2009 |
| DE | 202008017353 U1 | 7/2009 |
| EP | 2025324 A1 | 2/2009 |
| WO | 90/00894 | 2/1990 |
| WO | 95/00106 | 1/1995 |
| WO | 97/46231 | 12/1997 |
| WO | WO0006111 | 2/2000 |
| WO | 00/27353 | 5/2000 |
| WO | 01/05366 A1 | 1/2001 |
| WO | 2007/128776 A1 | 11/2007 |

OTHER PUBLICATIONS

International Search Report PCT/EP2010/064083 with Date of mailing Mar. 28, 2011.
Co-pending Application—Polonka et al.—Filed; Nov. 4, 2009; entitled Enhanced Photo Protection, U.S. Appl. No. 12/611,942.
Co-pending Application—Polonka et al.—Filed; Nov. 4, 2009, entitled Sunscreen Composition with Fatty Acid Alkanolamides, U.S. Appl. No. 12/611,943.

* cited by examiner

*Primary Examiner* — Sharmila G. Landau
*Assistant Examiner* — Barbara Frazier
(74) *Attorney, Agent, or Firm* — Milton L. Honig

(57) ABSTRACT

A cosmetic composition is provided including a water-insoluble UV-A sunscreen agent having a $\lambda_{max}$ at 330-380 nm, a water-insoluble UV-B sunscreen agent having a $\lambda_{max}$ between 280 and 320 nm, and a water-soluble sunscreen agent having a $\lambda_{max}$ between 280 and 400 nm, the water-soluble sunscreen agent being neutralized with metallic counter ions which in a first portion are sodium and in a second portion are potassium ions present in a respective molar ratio of 0.5:2 to 2:1, and a cosmetically acceptable carrier including from 0.2 to 4% of potassium stearate by weight of the composition.

8 Claims, No Drawings

SUNSCREEN COMPOSITION

BACKGROUND OF THE INVENTION

1. Field of the Invention

The invention concerns cosmetic compositions with enhanced photoprotection properties.

2. The Related Art

Many people dislike northern climates. There is a longing to bask in the warmth of the sun. Days at the beach find us in swimsuit attire. Many seek to turn their pale winter skin into a bronzed appearance. Others of naturally darker skin simply enjoy the refreshment of the seashore. Without protection from harmful ultraviolet radiation damage, these pleasures can turn into premature aging. Skin can loose elasticity and wrinkles appear in the premature aging process. Radiation can promote erythemal damage, can cause photo allergic reactions, and is implicated in skin cancers.

Protective measures are necessary. Lotions and creams formulated with sunscreens can shield against ultraviolet damaging radiation. The extent of protection varies widely.

Numerous ultraviolet photoprotective (sunscreen) agents are known. Nonetheless, only a small number are both commercially available and approved by regulatory authorities. A need exists to operate with known approved commercial sunscreen agents yet formulating them to achieve more than their expected level of photoprotection.

Representative of the art is U.S. Pat. No. 5,961,961 (Dobkowski et al.) reporting enhancement of the photoprotective effect by utilizing relatively large particle size titanium dioxide coupled with an organic sunscreen agent. Representative organic sunscreen agents include Benzophenone-3, octyl salicylate, octyl methoxycinnamate and 2-phenylbenzimidazole-5-sulphonic acid.

Certain types of cosmetic systems are particularly difficult to adequately fortify with photoprotective agents. A particular example is that of stearate structured gel systems containing small amounts of potassium stearate.

SUMMARY OF THE INVENTION

A cosmetic composition is provided which includes:
(i) a water-insoluble UV-A sunscreen agent having a $\lambda_{max}$ ranging from 330 to 380 nm;
(ii) a water-insoluble UV-B sunscreen agent having a $\lambda_{max}$ between 280 and 320 nm;
(iii) a water-soluble sunscreen agent having a $\lambda_{max}$ between 280 and 400 nm, the water-soluble sunscreen agent having metallic counter ions which in a first portion are sodium ions and in a second portion are potassium ions, the ions being in a respective molar ratio of 0.5:2 to 2:1; and
(iv) a cosmetically acceptable carrier including from 0.2 to 4% of potassium stearate by weight of the composition.

DETAILED DESCRIPTION OF THE INVENTION

Now it has been found that photoprotection can be enhanced by a cocktail of three different sunscreen agents, one of which is a water-soluble substance complexed with a metallic counter ion. A first portion of the water-soluble sunscreen agent (which will have a carboxylic or sulphonic acid function) will be neutralized by a sodium counter ion and a second portion of the water-soluble sunscreen agent will be neutralized by a potassium counter ion.

Cosmetic compositions of the present invention will include as a first element a UV-A sunscreen agent having a $\lambda_{max}$ between 330 and 380 nm. Particularly the $\lambda_{max}$ will range from 340 to 360 nm, and optimally at 360 nm. In this category of sunscreen agent, the preferred materials are 4,4'-t-butyl methoxydibenzoylmethane known as Avobenzone (available as Parsol 1789®), 2-hydroxy-4-methoxybenzophenone known as Benzophenone-3 and as Oxybenzone, terephthalylidene dicamphor sulfonic acid (available as Mexoryl SX) and combinations thereof.

Amounts of the water-insoluble UV-A sunscreen agent may range from 1 to 4%, optimally from 2 to 3% by weight of the composition.

A second element of the present invention is a water-insoluble UV-B sunscreen agent having a $\lambda_{max}$ ranging between 280 and 320 nm. More particularly the $\lambda_{max}$ may range from 300 to 310 nm, and optimally at 305 nm.

A large variety of substances may be utilized as the UV-B sunscreen agent. Illustrative are 2-ethylhexyl p-methoxycinnamate, octyldimethyl p-aminobenzoic acid, digalloyltrioleate, ethyl 4-[bis(hydroxypropyl)]aminobenzoate, 2-ethylhexyl-2-cyano-3,3-diphenylacrylate, octylsalicylate, glyceryl p-aminobenzoate, 3,3,5-trimethylcyclohexylsalicylate, methylanthranilate, p-dimethylaminobenzoic acid or aminobenzoate, 2-ethylhexyl p-dimethylaminobenzoate, bisethylhexyloxyphenol methoxyphenol triazine, methylene bis-benzotriazolyl tetramethylbutylphenol, dimethicodiethylbenzal malonate, isoamyl methoxycinnamate, octyl triazone, and mixtures thereof.

Amounts of the water-insoluble UV-B sunscreen agent may range from 1 to 8%, preferably from 3 to 6%, and optimally about 5% by weight of the composition. Most preferred is octyl salicylate.

Most preferred for purposes of this invention are compositions utilizing 3% Avobenzone and 4-5% octylsalicylate. Also useful is a combination of 2% Avobenzone and 5% octylsalicylate. These combinations are best joined with 2-phenylbenzimidazole-5-sulfonic acid or salts forms (available as Ensulizole®) in an amount of about 3%.

Advantageously but not necessarily the amount of water-insoluble UV-A to UV-B sunscreen agent may range from about 1:5 to 1:1, more preferably from 3:5 to 4:5 by weight of the composition.

A third type of photoprotection is provided by a water-soluble sunscreen agent having a $\lambda_{max}$ between 280 and 400 nm. Especially useful for this purpose is 2-phenylbenzimidazole-5-sulfonic acid and salt forms. Amounts of the water-soluble sunscreen agent may range from 1 to 4%, preferably from 2 to 3%, and optimally about 3% by weight of the composition.

Salt forms of the water-soluble further sunscreen agent will have a metallic counter ion which may be mixtures of sodium and potassium counter ions. These counter ions may be present in a relative molar ratio sodium to potassium of 0.5:2 to 2:1, preferably 0.8:2 to 1.5:1, more preferably from 0.8:1 to 1:1. Sodium and potassium in the preferred embodiments may be present in a relative weight ratio of 0.5:1 to 2:1, preferably 0.8:2 to 1.5:1, and more preferably from 0.8:1 to 0.4:1.

Cosmetic compositions of the present invention ordinarily will be in cream or lotion form. These will feature a cosmetically acceptable carrier, particularly a carrier that includes a stearate crystalline gel structurant system which contains small amounts of potassium stearate. Amounts of potassium stearate may range from 0.2 to 4%, preferably from 0.6 to 3%, and optimally from 1 to 2.5% by weight of the composition.

In addition to potassium stearate, the stearate crystalline gel structurant system may comprise a surfactant and co-surfactant. The nature of the surfactant and co-surfactant will depend upon whether the crystalline gel structurant is anionic or nonionic. Nonionic type crystalline gel structurant will have a surfactant and a co-surfactant different than that for the anionic systems. Preferred nonionic structurant surfactants are $C_1$-$C_{200}$ esters of $C_{10}$-$C_{22}$ fatty acid. Esters of the fatty acid preferably are polyol esters such as $C_2$-$C_3$ alkoxylated alcohol esters. Among these are the polyethoxy, polypropoxy and block polyethyoxy/polypropoxy alcohol esters. Particularly preferred are such esters as PEG-100 stearate, PEG-20 stearate, PEG-80 laurate, PEG-20 laurate, PEG-100 palmitate, PEG-20 palmitate and combinations thereof.

The co-surfactant of a nonionic structurant typically may be a combination of a $C_{10}$-$C_{22}$ fatty alcohol, glyceryl esters of a $C_{10}$-$C_{22}$ fatty acid, and a $C_{10}$-$C_{22}$ unesterified fatty acid. Relative amounts of the ester to the alcohol may range from about 100:1 to about 1:100, preferably from about 50:1 to about 1:50, and optimally from about 3:1 to about 1:3 by weight. Relative amounts of the combination of glyceryl ester and fatty alcohol to unesterified fatty acid may range from about 100:1 to about 1:100, preferably from about 50:1 to about 1:50, and optimally from about 3:1 to about 1:3 by weight. Typical fatty alcohols include behenyl alcohol, stearyl alcohol, cetyl alcohol, myristyl alcohol, lauryl alcohol, oleyl alcohol and combinations thereof.

The relative amount of surfactant and co-surfactant in a nonionic structurant may range from about 50:1 to about 1:50, preferably from about 10:1 to about 1:10, and optimally from about 3:1 to about 1:3 by weight.

For structurants that are anionic, the preferred surfactants are $C_{10}$-$C_{22}$ fatty acids and salts (i.e. soap) thereof and particularly combinations of these materials. Typical counterions forming the fatty acid salt are those of ammonium, sodium, potassium, lithium, trialkanolammonium (e.g. triethanolammonium) and combinations thereof. Amounts of the fatty acid to the fatty acid salt when both present may range from about 100:1 to about 1:100, preferably from about 50:1 to about 1:50, and optimally from about 3:1 to about 1:3 by weight. Illustrative fatty acids include behenic acid, stearic acid, isostearic acid, myristic acid, lauric acid, oleic acid, hydroxystearic acid and combinations thereof. Most preferred is stearic acid, particularly in amounts from 1 to 20% by weight of the composition. Among the fatty acid salts the most preferred is potassium stearate.

The co-surfactant for an anionic crystalline gel structurant typically is a $C_{10}$-$C_{22}$ fatty alcohol, a $C_1$-$C_{200}$ ester of a $C_{10}$-$C_{22}$ fatty acid and particularly combinations of these materials. Relative amounts of the ester to the alcohol when both present may range from about 100:1 to about 1:100, preferably from about 50:1 to about 1:50, and optimally from about 3:1 to about 1:3 by weight. Typical fatty alcohols include behenyl alcohol, stearyl alcohol, cetyl alcohol, myristyl alcohol, lauryl alcohol, oleyl alcohol and combinations thereof. Esters of the fatty acid preferably are polyol esters such as $C_2$-$C_3$ alkoxylated alcohol esters. Among these are the polyethoxy, polypropoxy and block polyethyoxy/polypropoxy alcohol esters. Particularly preferred are such esters as PEG-100 stearate, PEG-20 stearate, PEG-80 laurate, PEG-20 laurate, PEG-100 palmitate, PEG-20 palmitate and combinations thereof.

The relative amount of surfactant and co-surfactant for the anionic structurant may range from about 50:1 to about 1:50, preferably from about 10:1 to about 1:10, and optimally from about 3:1 to about 1:3 by weight.

The carrier may be present in amounts ranging from about 5 to about 98%, preferably from about 20 to about 95%, optimally from about 40 to about 80% by weight of the cosmetic compositions.

Water is the most common carrier component for this invention. Oily carrier components in the presence of water and an emulsifier will form emulsion systems as carriers. These systems may either be water-in-oil or oil-in-water emulsions. Besides water, suitable carrier classes include silicones, polyhydric alcohols, fatty alcohols, hydrocarbons, triglycerides and thickening powders.

Concentrations of the silicone may range from about 5% to about 60%, more preferably from about 5% to about 40%, by weight of the composition. These silicone fluids may be organic, silicone-containing or fluorine-containing, volatile or non-volatile, polar or non-polar.

Particularly preferred volatile silicone oils are cyclic volatile silicones wherein the repeating unit ranges from about 3 to about 5; and linear silicones wherein the repeating unit ranges from about 1 to about 7. Highly preferred examples of volatile silicone oils include cyclomethicones of varying viscosities, e.g., Dow Corning 200, Dow Corning 244, Dow Corning 245, Dow Corning 344, and Dow Corning 345, (commercially available from Dow Corning Corp.); SF-1204 and SF-1202 Silicone Fluids, GE 7207 and 7158 (commercially available from G.E. Silicones) and SWS-03314 (commercially available from SWS Silicones Corp.

Hydrocarbons may be useful as cosmetically acceptable carriers for compositions of this invention. They may include mineral oil, petrolatum and polyalpha-olefins. Examples of preferred volatile hydrocarbons include polydecanes such as isododecane and isodecane (e.g., Permethyl-99A which is available from Presperse Inc.) and the C7-C8 through C12-C15 isoparaffins (such as the Isopar Series available from Exxon Chemicals).

Polyhydric alcohols may serve as carriers. Illustrative of this group are propylyene glycol, dipropylene glycol, polypropylene glycol, polyethylene glycol, sorbitol, hydroxypropyl sorbitol, hexylene glycol, 1,3-butylene glycol, isoprene glycol, ethoxylated glycerol, propoxylated glycerol and mixtures thereof. Most preferred is glycerol known also as glycerin.

Fatty alcohols may also be useful carriers. The term "fatty" refers to carbon chain lengths ranging from 10 to 30 carbon atoms. Illustrative of this category are lauryl alcohol, cetyl alcohol, stearyl alcohol, isostearyl alcohol and combinations thereof.

Triglycerides are another group of materials useful as carriers. Illustrative but not limiting are sunflower seed oil, cotton oil, canola oil, soybean oil, castor oil, borage oil, olive oil, shea butter, jojoba oil and mixtures thereof. Mono- and di-glycerides may also be useful. Illustrative of these categories are glyceryl monostearate and glyceryl distearate.

Cosmetic compositions of the present invention may contain a variety of optional components to enhance physical properties and performance.

The optional components, when incorporated into the cosmetic compositions, should be suitable for use in contact with human keratinous tissue without undue toxicity, incompatibility, instability, allergic response, and the like within the scope of sound judgment. The *CTFA Cosmetic Ingredient Handbook*, Second Edition (1992) describes a wide variety of nonlimiting cosmetic and pharmaceutical ingredients commonly used in the skin care industry, which are suitable for use in the compositions of the present invention. Examples of these classes include: abrasives, absorbents, aesthetic components such as fragrances, pigments, colorings/colorants, essential oils, skin sensates, astringents, etc. (e.g. clove oil, menthol, camphor, eucalyptus oil, eugenol, menthyl lactate, witch hazel distillate), anti-acne agents, anti-caking agents, antifoaming agents, antimicrobial agents, antioxidants, biological additives, buffering agents, bulking agents, chelating agents, chemical additives, colorants, cosmetic astringents, cosmetic biocides, denaturants, drug astringents, external analgesics, film forming polymers, opacifying agents, pH adjusters, propellants, reducing agents, sequestrants, skin bleaching and lightening agents, skin conditioning agents, skin soothing and/or healing agents and derivatives, skin treating agents, thickeners, and vitamins and derivatives thereof.

A safe and effective amount of an anti-oxidant/radical scavenger may be added in amounts from about 0.01% to about 10%, more preferably from about 0.1% to about 5% by weight of the composition.

Anti-oxidants/radical scavengers may be employed such as ascorbic acid (vitamin C) and its salts, ascorbyl esters of fatty acids, ascorbic acid derivatives (e.g. magnesium ascorbyl phosphate), tocopherol (vitamin E), tocopherol sorbate, tocopherol acetate, other esters of tocopherol, butylated hydroxy benzoic acids and their salts, 6-hydroxy-2,5,7,8-tetramethylchroman-2-carboxylic acid (commercially available under the tradename Trolor®), amines (e.g. N,N-diethylhydroxylamine, amino-guanidine), nordihydroguaiaretic acid, bioflavonoids, amino acids, silymarin, tea extracts, and grape skin/seed extracts. Preferred anti-oxidants/radical scavengers are selected from esters of tocopherol, more preferably tocopherol acetate.

The cosmetic compositions may optionally comprise a flavonoid compound. Flavonoids are disclosed in U.S. Pat. Nos. 5,686,082 and 5,686,367 herein incorporated by reference. Examples of flavonoids particularly suitable flavones, isoflavones, coumarins, chromones, discoumarols, chromanones, chromanols, isomers (e.g. cis/trans isomers) thereof, and mixtures thereof.

Preferred for use are flavones and isoflavones, in particular daidzein (7,4'-dihydroxy isoflavone), genistein (5,7,4'-trihydroxy isoflavone), equol (7,4'-dihydroxy isoflavan), 5,7-dihydroxy-4'-methoxy isoflavone, soy isoflavones (a mixture extracted from soy), and mixtures thereof. Flavonoid compounds useful herein are commercially available from a number of sources, e.g., Indofine Chemical Company, Inc., Stearloids, Inc., and Aldrich Chemical Company, Inc. The herein described flavonoid compounds are preferably present in from about 0.01% to about 20%, more preferably from about 0.1% to about 10%, and even more preferably from about 0.5% to about 5% by weight.

Anti-inflammatory agents useful herein include allantoin and compounds of the Licorice (the plant genus/species *Glycyrrhiza glabra*) family, including glycyrrhetic acid, glycyrrhizic acid, and derivatives thereof (e.g. salts and esters).

The compositions may comprise a tanning active. When present, it is preferable that the compositions comprise from about 0.1% to about 20%, more preferably from about 2% to about 7% by weight of the composition. A preferred tanning active is dihydroxyacetone.

The compositions may comprise a skin lightening agent. When used, the compositions preferably comprise from about 0.1% to about 10%, more preferably from about 0.2% to about 5%, also preferably from about 0.5% to about 2%, by weight of the composition, of a skin lightening agent. Suitable skin lightening agents include niacinamide, kojic acid, arbutin, tranexamic acid, placental extract, ascorbic acid and derivatives thereof (e.g. magnesium ascorbyl phosphate, sodium ascorbyl phosphate, ascorbyl glucoside, and ascorbyl tetraisopalmitates). Other skin lightening materials suitable for use herein include Actiwhite® (Cognis), Emblica® (Rona), Azeloglicina (Sinerga) and extracts (e.g. mulberry extract).

The compositions may comprise an antimicrobial or antifungal active. Such actives are capable of destroying microbes, preventing the development of microbes or preventing the pathogenic action of microbes. A safe and effective amount of an antimicrobial or antifungal active may be added to the present compositions, preferably, from about 0.001% to about 10%, more preferably from about 0.01% to about 5%, and even more preferably from about 0.05% to about 2% by weight of the composition.

Preferred examples of these actives include those selected from the group consisting of salicylic acid, benzoyl peroxide, 3-hydroxy benzoic acid, glycolic acid, lactic acid, 4-hydroxy benzoic acid, acetyl salicylic acid, 2-hydroxybutanoic acid, 2-hydroxypentanoic acid, 2-hydroxyhexanoic acid, cis-retinoic acid, trans-retinoic acid, retinol, phytic acid, N-acetyl-L-cystein, lipoic acid, azelaic acid, arachidonic acid, benzoylperoxide, tetracycline, ibuprofen, naproxen, hydrocortisone, acetominophen, resorcinol, phenoxyethanol, phenoxypropanol, phenoxyisopropanol, 2,4,4'-trichloro-2'-hydroxy diphenyl ether, 3,4,4'-trichlorocarbanilide, octopirox, ciclopirox, lidocaine hydrochloride, clotrimazole, climbazole, miconazole, ketoconazole, neocycin sulfate, and mixtures thereof.

The compositions may comprise a conditioning agent selected from the group consisting of humectants, moisturizers, or skin conditioners. A variety of these materials can be employed and each can be present at a level of from about 0.01% to about 40%, more preferably from about 0.1% to about 30%, and even more preferably from about 0.5% to about 15% by weight of the composition. These materials include, but are not limited to, guanidine; urea; glycolic acid and glycolate salts (e.g. ammonium and quaternary alkyl ammonium); lactic acid and lactate salts (e.g. ammonium and quaternary alkyl ammonium); aloe vera in any of its variety of forms (e.g., aloe vera gel); polyhydroxy compounds such as sorbitol, mannitol, glycerol, hexanetriol, butanetriol, propylene glycol, butylene glycol and hexylene glycol; polyethylene glycols; sugars and starch derivatives (e.g. alkoxylated glucose, fructose, sucrose, trehalose); hyaluronic acid; lactamide monoethanolamine; acetamide monoethanolamine; sucrose polyester; petrolatum; and mixtures thereof.

Except in the operating and comparative examples, or where otherwise explicitly indicated, all numbers in this description indicating amounts of material ought to be understood as modified by the word "about".

The term "comprising" is meant not to be limiting to any subsequently stated elements but rather to encompass non-specified elements of major or minor functional importance. In other words the listed steps, elements or options need not be exhaustive. Whenever the words "including" or "having" are used, these terms are meant to be equivalent to "comprising" as defined above.

All documents referred to herein, including all patents, patent applications, and printed publications, are hereby incorporated by reference in their entirety in this disclosure.

The following examples will more fully illustrate the embodiments of this invention. All parts, percentages and proportions referred to herein and in the appended claims are by weight unless otherwise illustrated.

EXAMPLES 1-8

A series of compositions are outlined in Table I which are illustrative of the present invention.

TABLE I

| Component | \multicolumn{8}{c}{Sample No. (Weight %)} | | | | | | | |
|---|---|---|---|---|---|---|---|---|
| | 1 | 2 | 3 | 4 | 5 | 6 | 7 | 8 |
| Stearic Acid | 15.0 | 15.0 | 5.0 | 10.0 | 10.0 | 8.0 | 8.0 | 8.0 |
| Stearamide AMP/Glycol Stearate | 8.0 | 8.0 | 5.0 | 5.0 | 8.0 | 8.0 | 8.0 | 8.0 |
| Glycerol Monostearate | 2.5 | 4.5 | 1.5 | 1.5 | 2.5 | 2.5 | 2.5 | 2.5 |
| Cetyl Alcohol | 1.5 | 0.5 | 0.5 | 1.0 | 1.0 | 1.0 | 1.0 | 1.0 |
| PEG-100 Stearate | 1.5 | 2.5 | 1.5 | 2.5 | 2.5 | 2.5 | 1.5 | 1.5 |
| Potassium Stearate | 1.0 | 1.5 | 0.8 | 0.8 | 3.0 | 1.5 | 1.5 | 1.1 |
| Avobenzone | 2.0 | 2.0 | 3.0 | 3.0 | 2.0 | 2.0 | 3.0 | 3.0 |
| Octyl Salicylate | 5.0 | 5.0 | 5.0 | 5.0 | 5.0 | 5.0 | 5.0 | 5.0 |
| Sodium 2-Phenylbenzimidazole-5-sulfonate | 1.2 | 1.2 | 1.2 | 0.9 | 1.2 | 1.2 | 1.5 | 1.0 |
| Potassium 2-Phenylbenzimidazole-5-sulfonate | 2.0 | 2.0 | 1.8 | 1.8 | 1.2 | 1.2 | 1.5 | 1.5 |
| Glycerin | 5.0 | 5.0 | 5.0 | 5.0 | 5.0 | 5.0 | 5.0 | 5.0 |
| Silicone Oil | 0.5 | 0.5 | 0.5 | 0.5 | 0.5 | 0.5 | 0.5 | 0.5 |
| Isopropyl Myristate | 0.75 | 0.75 | 0.75 | 0.75 | 0.75 | 0.75 | 0.75 | 0.75 |
| Methyl Paraben | 0.15 | 0.15 | 0.15 | 0.15 | 0.15 | 0.15 | 0.15 | 0.15 |
| Propyl Paraben | 0.15 | 0.15 | 0.15 | 0.15 | 0.15 | 0.15 | 0.15 | 0.15 |
| Water | to 100 | to 100 | to 100 | to 100 | to 100 | to 100 | to 100 | to 100 |

The salts in Table I are generated by neutralizing stearic acid and 2-phenylbenzimidazole sulfonic acid in situ with an appropriate amount of sodium hydroxide and potassium hydroxide.

EXAMPLE 9

Photoprotective effects were evaluated on a model system wherein the lamellar oil phase of an aqueous emulsion had the formula outlined in Table II. Weight percentages are on the basis of the total emulsion composition.

TABLE II

| Component | Weight % |
|---|---|
| Stearic Acid | 1.58 |
| Glycol Stearate/Stearamide AMP | 1.74 |
| Glyceryl Monostearate | 0.81 |
| Cetyl Alcohol | 0.47 |
| PEG-100 Stearate | 1.50 |
| Avobenzone | 3.00 |
| Octyl Salicylate | 5.00 |
| 2-Phenylbenzimidazole-5-sulfonic acid (in aqueous phase) | 3.00 |

Into the base formula were added different amounts of neutralizing agent to evaluate the effect of sodium, potassium and triethanolammonium (TEA) counter ions.

Procedure

SPF Measurements

Sun protection factor (SPF) was measured in vitro using an Optometrics SPF 290 instrument. The test procedure required calibration of the monochrometer and sample stage of the Optometrics SPF 290 instrument. Thereafter the instrument was calibrated with a blank sample quartz plate (10 cm×10 cm and 3 mm thickness). Calibration zeros the UV detector. Formulas were applied and spread uniformly onto a plate to leave a film of 2 mg/cm². The film was left to dry for 30 minutes. Subsequently an SPF reading was taken on the dried film using three measurements on different parts of the coated quartz plate and recording an average value.

MPF is equivalent to the SPF value at a specific wavelength. For the present experiments the wavelength is the peak maximum at 305 to 360 nm.

Results

Table III outlines the effects of using different neutralizers against the water-soluble sulfonic acid unit of 2-phenylbenzimidazol-5-sulfonic acid sunscreen.

TABLE III

| | \multicolumn{6}{c}{UV Absorption Data} | | | | | |
| | \multicolumn{3}{c}{Weight %} | In-vitro | Intensity $\lambda_{max}$ = 305 nm | Intensity $\lambda_{max}$ = 360 nm |
| Sample | TEA | NaOH | KOH | SPF | (MPF) | (MPF) |
|---|---|---|---|---|---|---|
| 1 | 3.80 | — | — | 23.4 | 49.4 | 10.6 |
| 2 | 1.90 | — | — | 17.1 | 30.1 | 4.6 |
| 3 | — | — | 1.86 | 18.4 | 27.4 | 17.4 |
| 4 | — | 1.46 | — | 12.1 | 26.2 | 5.2 |
| 5 | 2.50 | 0.80 | — | 21.4 | 50.2 | 4.9 |
| 6 | 1.00 | 0.86 | — | 25.3 | 52.2 | 6.7 |
| 7 | 2.50 | — | 1.00 | 22.6 | 48.6 | 13.1 |
| 8 | — | 1.36 | 0.50 | 14.2 | 27.8 | 10.0 |
| 9 | — | 0.86 | 1.00 | 30.1 | 63.1 | 20.1 |
| 10 | — | 0.61 | 1.25 | 28.1 | 64.1 | 19.6 |

Triethanolamine (TEA) neutralized sulfonic acid functionalized sunscreen agent formulated in Sample 1 gave good photoprotection results. Nonetheless, the system is operative only with high levels of TEA. The "higher" UVA intensity at $\lambda_{max}$ 360 nm (10.6 int value) is achieved only after rub-in of the sample. Application without rub-in does not achieve the same good result. Sample 2 illustrates a TEA only system with neutralizer level at half that of Sample 1. The result was much lower photoprotection.

Sample 3 is a formula neutralized only with potassium hydroxide. SPF and intensity at 305 nm was substantially equivalent to the TEA neutralized Sample 2. However, there was a significant improvement in the $\lambda_{max}$ at 360 nm with a reading of 17.4.

Sample 4 is a formula neutralized only with sodium hydroxide. UV absorption is relatively poor. The SPF amounts to only 12.1. The $\lambda_{max}$ UV absorption intensity at 305 nm and 360 nm were only 26.2 and 5.2, respectively.

Samples 5 and 6 are the base formula neutralized with a combination of TEA and sodium hydroxide. Much better performance is seen in contrast to utilizing solely a sodium hydroxide neutralized system. However, the $\lambda_{max}$ at 360 nm of 4.9 and 6.7, respectively, were relatively modest. This means that UV-A performance needs improvement.

Sample 7 is a formula wherein TEA and potassium hydroxide were utilized as neutralization agents. Results are similar to that obtained with Sample 1, but with a slightly enhanced UV-A response of 13.1.

Sample 8 illustrates a mixture of sodium hydroxide and potassium hydroxide neutralized base formula. Sodium hydroxide was present in greater than twice the amount of potassium hydroxide. The UV absorption data was inferior to Samples 1 and 2.

Samples 9 and 10 neutralized predominantly with potassium hydroxide and to a lesser level with sodium hydroxide are representative of the present invention. SPF dramatically increased to 30.1 and 28.1, respectively. The $\lambda_{max}$ at 305 nm provided respective MPF intensity values of 63.1 and 64.1. These values were exceptional. Furthermore, the intensities at $\lambda_{max}$ 360 nm were the best from all ten samples, being respectively 20.1 and 19.6.

What is claimed is:

1. A cosmetic composition comprising:
   (i) a water-insoluble UV-A sunscreen agent having a $\lambda_{max}$ ranging from 330 to 380 nm;
   (ii) a water-insoluble UV-B sunscreen agent having a $\lambda_{max}$ between 280 and 320 nm;
   (iii) a water-soluble sunscreen agent having a $\lambda_{max}$ between 280 and 400 nm, the water-soluble sunscreen agent being 2-phenylbenzimidazole-5-sulfonic acid salt, the salt in a first portion having sodium ions and in a second portion having potassium ions, the ions being in a respective molar ratio of 0.4:1 to 1:1; and
   (iv) a cosmetically acceptable carrier comprising from 0.2 to 4% of potassium stearate by weight of the composition.

2. The composition according to claim 1 wherein the water-insoluble UV-A sunscreen agent and water-insoluble UV-B sunscreen agent are present in a relative weight ratio of from 1:5 to 1:1.

3. The composition according to claim 1 wherein the carrier comprises a stearate gel crystalline structurant system.

4. The composition according to claim 1 wherein the water-insoluble UV-A sunscreen agent is selected from the group consisting of Avobenzone, Benzophenone-3 and mixtures thereof.

5. The composition according to claim 4 wherein the water-insoluble UV-B sunscreen agent is selected from octyl methoxycinnamate, octyl salicylate and mixtures thereof.

6. The composition according to claim 1 wherein the carrier further comprises from 1 to 20% of stearic acid by weight of the composition.

7. The composition according to claim 1 wherein the water-insoluble UV-A sunscreen agent and the water-soluble sunscreen agent are each present in an amount from 1 to 4% by weight of the composition.

8. The composition according to claim 1 wherein the water-insoluble UV-B sunscreen agent is present in an amount from 1 to 8% by weight of the composition.

* * * * *